US011426066B2

(12) United States Patent
Brocwell

(10) Patent No.: US 11,426,066 B2
(45) Date of Patent: Aug. 30, 2022

(54) ONLINE VISION TESTING

(71) Applicant: VPH Intellectual Property, LLC, Palm City, FL (US)

(72) Inventor: C. Brad Brocwell, Waynesville, OH (US)

(73) Assignee: VPH INTELLECTUAL PROPERTY, LLC, Palm Springs, FL (US)

( * ) Notice: Subject to any disclaimer, the term of this patent is extended or adjusted under 35 U.S.C. 154(b) by 416 days.

(21) Appl. No.: 16/735,673

(22) Filed: Jan. 6, 2020

(65) Prior Publication Data

US 2021/0204807 A1 Jul. 8, 2021

(51) Int. Cl.
*A61B 3/02* (2006.01)
*A61B 3/032* (2006.01)
*A61B 3/036* (2006.01)
*A61B 5/00* (2006.01)
*G06F 16/95* (2019.01)

(52) U.S. Cl.
CPC .............. *A61B 3/032* (2013.01); *A61B 3/036* (2013.01); *A61B 5/0022* (2013.01); *G06F 16/95* (2019.01)

(58) Field of Classification Search
CPC ....... A61B 3/032; A61B 3/036; A61B 5/0022; G06F 16/95

USPC ................. 351/211, 237, 239–244
See application file for complete search history.

(56) References Cited

U.S. PATENT DOCUMENTS

2004/0105073 A1\* 6/2004 Maddalena ............ A61B 3/032
351/205
2014/0268060 A1\* 9/2014 Lee ........................ A61B 3/032
351/241

\* cited by examiner

*Primary Examiner* — Mahidere S Sahle
(74) *Attorney, Agent, or Firm* — Shutts & Bowen LLP

(57) ABSTRACT

A selection for an acuity test chart is received in distributed Web content that correlates to a distance between an end user and a display of the test chart. A selection also is received of a trio of lines of different widths in a set of lines defining one of twelve radially equidistant radii of equal length extending from a common vertex in an astigmatism clock chart. An astigmatism fan chart also is generated and presented in the Web content utilizing three of the trio of lines in the selection and including twelve repeating sequences of three radially equidistant radii of different widths corresponding to the different widths of the utilized three of the trio of lines. One of the radii is selected and a prescription computed including the visual acuity value, a cylinder value deriving from the selected trio, and an axis value deriving from the selected radii.

15 Claims, 2 Drawing Sheets

ONLINE VISION TESTING

BACKGROUND OF THE INVENTION

Field of the Invention

The present invention relates to the field of online vision testing.

Description of the Related Art

An eyeglass refers to a spectacle that includes both a frame and also a pair of lenses disposed within the frame. The lenses tend to be prescriptive based upon the either single vision with one power from one edge of the lens to the other and address nearsightedness, farsightedness, or astigmatism, or progressive vision with provides two or three focal points in one lens to address both near sightedness and farsightedness in one lens. With respect to progressive lenses, bifocal lenses and trifocal lenses provide, respectively, two focal points—near and distance—or three focal points: near, mid-range and distance.

Each frame is able to accommodate a particular type of lens, but depending upon the thickness and shape of lens, in some instances, only some frames can accommodate some lenses. Thus, at the outset, one must select a lens in accordance with a personal prescription before selecting a frame from amongst a limited set of frames able to accommodate the selected lens. To do so can be time consuming and requiring substantive interaction with a sales associate in a retail setting. Yet, in the modern era, retail customers seeking to purchase custom eyeglasses lack the patience for such interactions and much prefer independent shopping without assistance from a sales associate. Indeed, while in-store shopping remains a prevalent mode for selecting eyeglasses for purchase, increasingly customers prefer remote shopping online over the global Internet.

Self-selecting eyeglasses in an online environment is not without its challenges. Indeed, part and parcel of proper eyeglass selection is the knowledge of the correct prescription including visual acuity, cylinder value and axis value. To acquire these values generally requires an on-site, offline visit to the optician or ophthalmologist. In particular, where it is known to acquire visual acuity online through the Web page presentation of an acuity test, ascertaining the axis and cylinder values associated with astigmatism is a more challenging proposition. Thus, online shopping for prescriptive glasses has not enjoyed the widespread adoption that otherwise would have occurred were online vision testing more accurate and readily accessible by the ordinary consumer.

BRIEF SUMMARY OF THE INVENTION

Embodiments of the present invention address deficiencies of the art in respect to vision testing for remotely disposed individuals and provide a novel and non-obvious method, system and computer program product for online vision testing for remotely disposed individuals. In an embodiment of the invention, an online vision testing method includes establishing a communicative connection between a host computing system and a client computing device from over a computer communications network. The method additionally includes distributing Web content from the host computing system to the client computing device, the Web content presenting an acuity test chart. The method further includes receiving as input in the Web content, a line selection corresponding to a visual acuity value.

The method yet further includes distributing from the host computing system to the client computing device, further Web content that presents an astigmatism clock chart of six intersecting sets of three lines of three different widths and of equal length. In the clock chart, the sets of three lines intersect at a midpoint of each of the sets of the three lines and are radially separated equidistantly. Thereafter, a first selection in the additional Web content may be received in respect to one of the sets of three lines. Responsive to this selection, yet further Web content may be distributed presenting an astigmatism fan chart of thirty-six equidistantly arranged radii from a single vertex. The radii include a repeating sequence of lines of identical width to the selected one of the sets of three lines. Subsequent to the presentation of the astigmatism fan chart, a second selection is received of one of the radii so as to identify a radial value for the second selection. Finally, an eyeglass prescription is presented to the client computing device including the visual acuity value, a cylinder value and an axis value, the cylinder and axis values deriving from the first and second selections.

In one aspect of the embodiment, the communicative connection is established through a display of a Web page in a Web browser in the client computing device, such that the host computing system transmits the Web page to the Web browser. As such, the Web page may include a selectable user interface control indicating the existence of a pre-stored prescription. In response to receiving such an indication, a pre-stored eyeglass prescription is retrieved that includes a pre-stored visual acuity value, pre-stored cylinder value and pre-stored axis value. These pre-stored values are then presented in the Web page in lieu of the presentation of the acuity chart and the astigmatism clock chart to derive the visual acuity value, cylinder value and axis value. In another aspect of the embodiment, the method additionally includes presenting through the Web page, a video conferencing portal over which verbal directives are presented. In this regard, the verbal directives may include directives for standing at a specified distance from the Web content.

In a different embodiment of the invention, an online vision testing includes establishing a communicative connection between a host computing system and a client computing device from over a computer communications network and distributing Web content from the host computing system to the client computing device. The Web content as distributed includes each of an acuity test chart and an astigmatism clock chart. Then, in response to the distribution of the Web content, two selections are received: (A) a selection for the acuity test chart correlative to a distance between an end user viewing the acuity test chart and a display of the acuity test chart in the client computing device, and (B) a selection of a trio of lines of different widths in a set of lines defining one of twelve radially equidistant radii of equal length extending from a common vertex in the astigmatism clock chart.

Even further, an astigmatism fan chart is generated and presented in the Web content utilizing three of the trio of lines in the selection. The fan chart includes twelve repeating sequences of three radially equidistant radii of different widths corresponding to the different widths of the utilized three of the trio of lines. Each of the lines of the fan chart includes an equal length and extends from a common vertex in the astigmatism fan chart. A selection is then received in response to the presentation of the fan chart, of one of the radii. Finally, an eyeglass prescription is both computed and displayed in the client computing device that includes the visual acuity value, a cylinder value and an axis value, with the cylinder value deriving from the selected trio of lines in the clock chart, and the axis value deriving from the selected one of the radii in the fan chart.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

Embodiments of the invention provide for online vision testing. In accordance with an embodiment of the invention, a content server in a remote online vision testing data processing system responds to different requests from different content browsers by presenting a series of vision tests within Web content to each requesting content browser. A first vision test is an acuity test visually disposed within Web content that also includes a user interface control operable to select a line of the acuity test for transmission back to the content server. A second vision test is an astigmatism clock chart that includes six intersecting trios of lines of varying widths and is visually disposed within Web content that also includes a user interface control operable to select one of the trio of lines for transmission back to the content server. A third vision test is an astigmatism fan chart of thirty-six equidistantly arranged radii from a single vertex with the radii including a repeating sequence of lines of identical width to the selected trio of lines and disposed within Web content that also includes a user interface control operable to select one of the radii in the fan chart to produce a radial value. In response to the varying selections in the Web content, prescription are able to be produced in Web content for delivery to the requesting clients including an acuity value, cylinder value and axis value.

Figure 1:
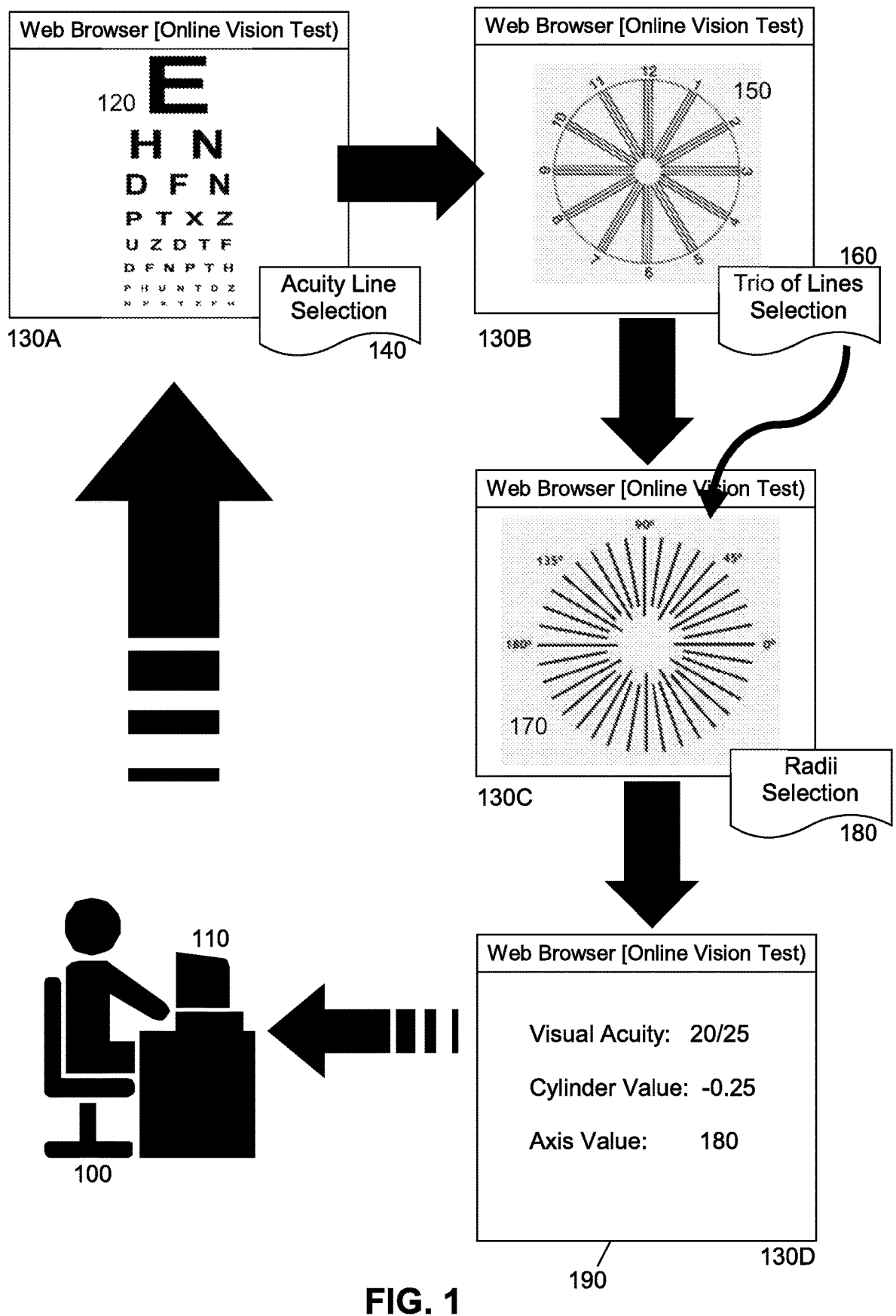
FIG. 1 is a pictorial illustration of a process for online vision testing.

In further illustration, FIG. 1 is a pictorial illustration of a process for online vision testing. As shown in FIG. 1, a consumer 100 acting through a client computing device 110 accesses a first Web page 130A that includes an acuity test 120. At a prescribed distance from the screen of the client computing device 110, the consumer 100 selects a line in the acuity test 120 so as to produce an acuity line selection 140 sufficient to determine a visual acuity of the consumer 100. Next, the consumer 100 accesses a second Web page 130B that includes an astigmatism clock chart 150 of six intersecting sets of three lines of three different widths and of equal length. In the clock chart 150, the sets of three lines intersect at a midpoint of each of the sets of the three lines and are radially separated equidistantly. The consumer 100 then selects one of the trio of lines to produce a selection 160. In response to this selection, the consumer 100 accesses a third Web page 130C that includes an astigmatism fan chart 170 of thirty-six equidistantly arranged radii from a single vertex. The radii include a repeating sequence of lines of identical width to the selection 160. The consumer 100 then selects one of the radii in the fan chart 170 to produce a radial value 180. Finally, a visual acuity is derived from the acuity line selection 140 along with a cylinder value and an axis value is derived from the radii selection 180 and presented as a prescription 190 within Web page 130D. In this way, an accurate determination of the prescription 190 including the axis value can be provided remotely, online without requiring the presence of the consumer 100 in a store so as to facilitate an online eyeglass shopping experience.

Figure 2:
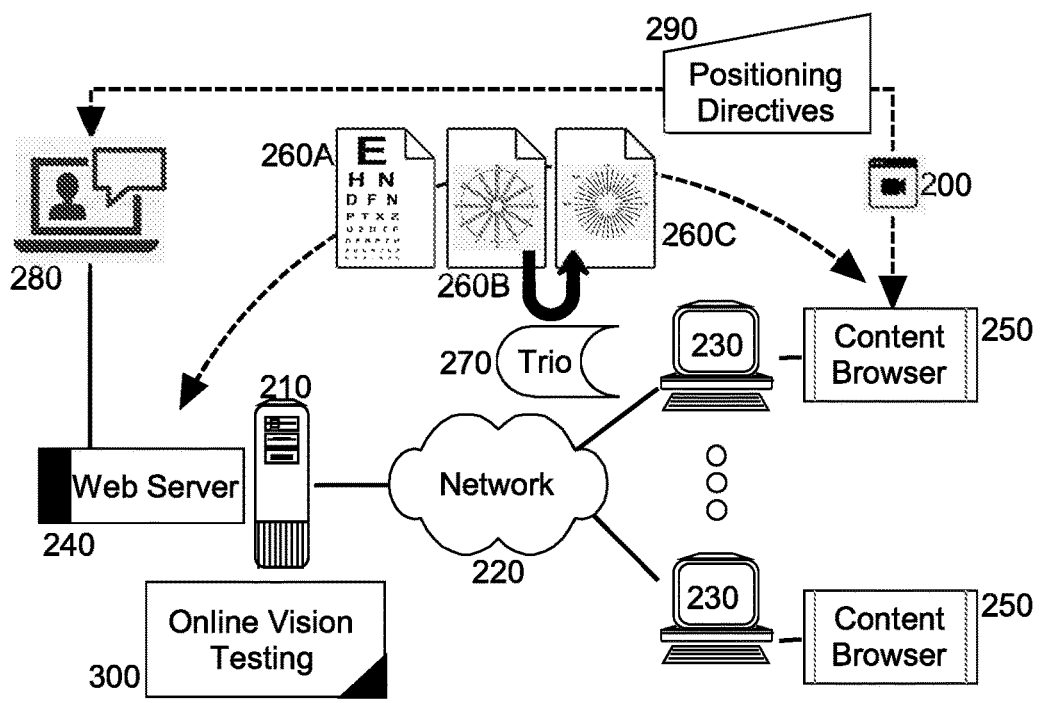
FIG. 2 is a schematic illustration of a data processing system configured for online vision testing; and, FIG. 3 is a flow chart illustrating a process for online vision testing.

The process described in connection with FIG. 1 may be implemented within a data processing system. In further illustration, FIG. 2 schematically shows a data processing system configured for online vision testing. The system includes a host computing system 210 that includes one or more computers, each with memory and at least one processor. The host computing system 210 supports the operation of a Web server 240 that in turn, is operable to receive Web content requests from over a computer communications network 220 from different content browsers 250 in respectively different client computers 230, and to provide responsive Web content to the Web content requests to the requesting ones of the content browsers 250.

Of import, an online vision testing module 300 is disposed in the host computing system 210. The online vision testing module 300 includes computer program instructions enabled during execution in the memory of the host computing system 210 to respond to a request from one of the content browsers 250 by supplying first Web content 260A including an acuity test for display in the one of the content browsers 250, and to receive in response, a selection of a line in the acuity test. Optionally, the program instructions transmit to communicatively linked video conferencing endpoint 280 an instruction to establish a Web conference 200 with the one of the content browsers 250 over which positioning directives 290 are provided so as to position an end user a prescribed distance from the content browser 250 during the acuity test.

The program instructions also are enabled to respond to the selection of the line in the acuity test by supplying second Web content 260B including an astigmatism clock chart for display in the one of the content browsers 250, and to receive in response, a selection of a trio of lines in the clock chart. The program instructions further are enabled to respond to the selection of the trio of lines in the clock chart by supplying third Web content 260C including an astigmatism fan chart constructed of radii based upon the widths of the selection of the trio of lines for display in the one of the content browsers 250, and to receive in response, a selection of one of the radii in the fan chart. Finally, the program instructions are enabled to present a prescription for vision including an acuity value from the acuity test, a cylinder value derived from the acuity test, and an axis value derived from the selected axis in the third Web content 260C.

Figure 3:
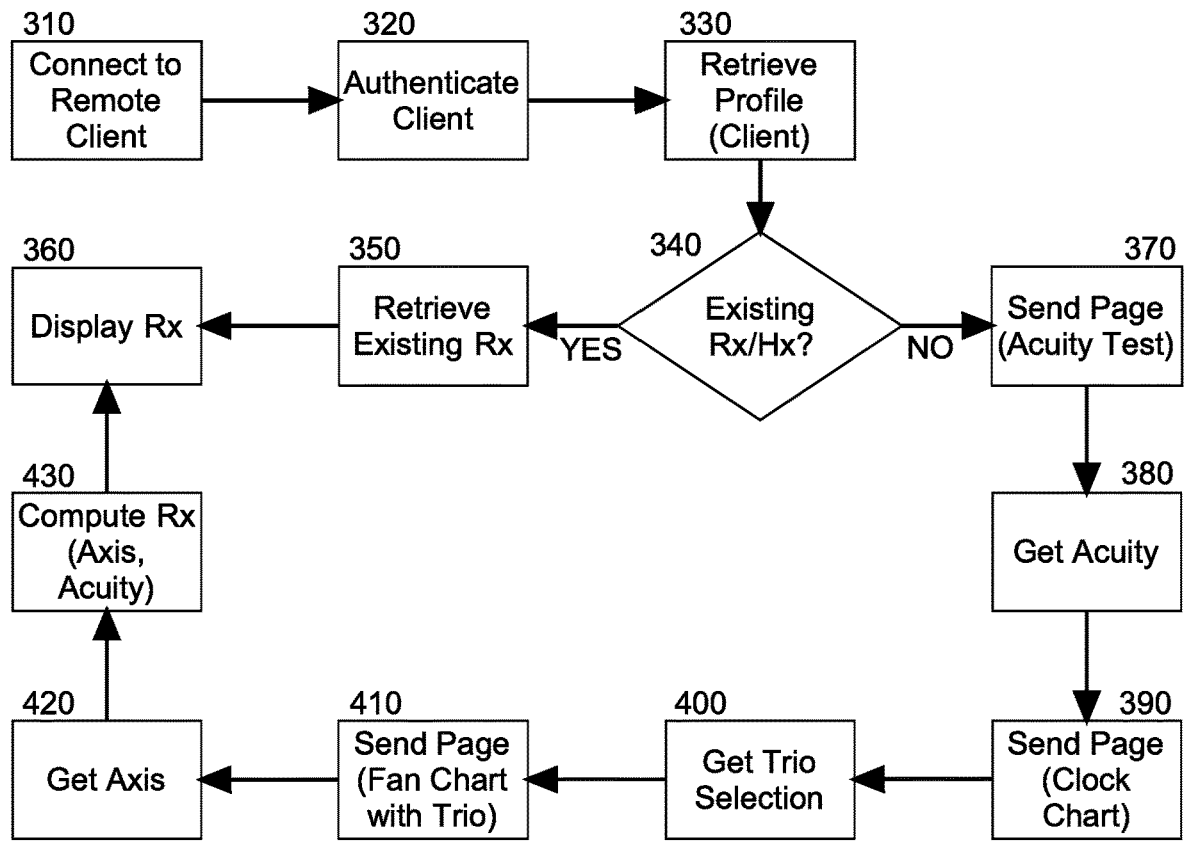

In even further illustration of the operation of the online vision testing module 300, FIG. 3 is a flow chart illustrating a process for online vision testing. Beginning in block 310, a connection is established as between the online vision testing data processing system and a remote client. In block 320, the remote client is authenticated and in block 330, a pre-stored profile for the client retrieved. In decision block 340, it is determined whether or not a pre-existing prescription is accessible for the authenticated client. If so, in block 350 the pre-existing prescription is retrieved and displayed in a user interface of the remote client in block 360. However, if it is determined in decision block 340 that no pre-existing prescription can be retrieved for the authenticated client, then the process continues in block 370.

In block 370, Web content is produced for inclusion in a Web page that incorporates an image of an acuity test of different lines, each line corresponding to a different acuity determination. The Web page is then transmitted to the remote client and, in response, in block 380 an acuity selection of a line in the acuity test is received and stored in memory for subsequent use in determining a cylinder value and an acuity value. Then, in block 390, additional Web content is produced for inclusion in either the same Web page or a different Web page, that incorporates an image of an astigmatism clock chart. In block 400, a selection of a particular trio of lines in the clock chart is received in the Web server and in block 410, yet further Web content is produced for inclusion either in the same Web page or a different Web page, that incorporates an image of an astigmatism fan chart with radii of widths determined in correspondence to the selected trio of lines of the clock chart. In block 420, a particular axis value is derived from a selection of one of the radii in the clock chart and, with the axis value, a prescription is computed in block 430. Finally, in block 360, the prescription is displayed as Web content in the same Web page, or in a different Web page.

The present invention may be embodied within a system, a method, a computer program product or any combination thereof. The computer program product may include a computer readable storage medium or media having computer readable program instructions thereon for causing a processor to carry out aspects of the present invention. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing.

Computer readable program instructions described herein can be downloaded to respective computing/processing devices from a computer readable storage medium or to an external computer or external storage device via a network. The computer readable program instructions may execute entirely on the user's computer, partly on the user's computer, as a stand-alone software package, partly on the user's computer and partly on a remote computer or entirely on the remote computer or server. Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which includes one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Finally, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Having thus described the invention of the present application in detail and by reference to embodiments thereof, it will be apparent that modifications and variations are possible without departing from the scope of the invention defined in the appended claims as follows:

1. An online vision testing method comprising:
   establishing a communicative connection between a host computing system and a client computing device from over a computer communications network;
   first distributing Web content from the host computing system to the client computing device, the Web content presenting an acuity test chart and receiving input indicating a line selection of the acuity test corresponding to a visual acuity value;
   second distributing further Web content from the host computing system to the client computing device, the further Web content presenting an astigmatism clock chart of six intersecting sets of three lines of three different widths and of equal length, the sets of three lines intersecting at a midpoint of each of the sets of the three lines and radially separated equidistantly;
   receiving a first selection in the additional Web content of one of the sets of three lines and third distributing yet further Web content presenting an astigmatism fan chart of thirty-six equidistantly arranged radii from a single vertex, the radii comprising a repeating sequence of lines of identical width to the selected one of the sets of three lines;
   receiving a second selection in the yet further Web content of one of the radii and identifying a radial value for the second selection; and,
   presenting an eyeglass prescription including the visual acuity value, a cylinder value and an axis value, the cylinder and axis values deriving from the first and second selections.

2. The method of claim 1, wherein the communicative connection is established through a display of a Web page in a Web browser in the client computing device, the host computing system transmitting the Web page to the Web browser.

3. The method of claim 2, wherein the Web page includes a selectable user interface control for a pre-stored prescription and in response to receiving a selection of the control, retrieving a pre-stored eyeglass prescription including a pre-stored visual acuity value, pre-stored cylinder value and pre-stored axis value in lieu of presenting the acuity chart and the astigmatism clock chart to derive the visual acuity value, cylinder value and axis value.

4. The method of claim 2, further comprising presenting through the Web page, a video conferencing portal over which verbal directives are presented.

5. The method of claim 4, wherein the verbal directives include directives for standing at a specified distance from the Web content.

6. An online vision testing method comprising:
   establishing a communicative connection between a host computing system and a client computing device from over a computer communications network;
   distributing Web content from the host computing system to the client computing device, the Web content comprising each of an acuity test chart and an astigmatism clock chart;
   receiving in response to the distribution of the Web content, (A) a selection for the acuity test chart correlative to a distance between an end user viewing the acuity test chart and a display of the acuity test chart in the client computing device, and (B) a selection of a trio of lines of different widths in a set of lines defining one of twelve radially equidistant radii of equal length extending from a common vertex in the astigmatism clock chart;
   generating and presenting in the Web content an astigmatism fan chart utilizing three of the trio of lines in the selection, the fan chart comprising twelve repeating sequences of three radially equidistant radii of different widths corresponding to the different widths of the utilized three of the trio of lines, each of the lines of the fan chart comprising an equal length and extending from a common vertex in the astigmatism fan chart;
   receiving in response to the presentation of the fan chart, a selection of one of the radii; and,
   computing and displaying in the client computing device an eyeglass prescription including the visual acuity value, a cylinder value and an axis value, the cylinder value deriving from the selected trio of lines in the clock chart, and the axis value deriving from the selected one of the radii in the fan chart.

7. The method of claim 6, wherein the communicative connection is established through a display of a Web page in a Web browser in the client computing device, the host computing system transmitting the Web page to the Web browser.

8. The method of claim 7, wherein the Web page includes a selectable user interface control for a pre-stored prescription and in response to receiving a selection of the control, retrieving a pre-stored eyeglass prescription including a pre-stored visual acuity value, pre-stored cylinder value and pre-stored axis value in lieu of presenting the acuity chart and the astigmatism clock chart to derive the visual acuity value, cylinder value and axis value.

9. The method of claim 7, further comprising presenting through the Web page, a video conferencing portal over which verbal directives are presented.

10. The method of claim 9, wherein the verbal directives include directives for standing at a specified distance from the Web content.

11. A vision testing data processing system comprising:
   a host computing system comprising one or more computers, each with memory and at least one processor; and,
   a remote vision testing module comprising computer program instructions enabled during execution in the host computing system to perform:
     establishing a communicative connection between the host computing system and a client computing device from over a computer communications network;
     first distributing Web content from the host computing system to the client computing device, the Web content presenting an acuity test chart and receiving input indicating a line selection of the acuity test corresponding to a visual acuity value;
     second distributing further Web content from the host computing system to the client computing device, the further Web content presenting an astigmatism clock chart of six intersecting sets of three lines of three different widths and of equal length, the sets of three lines intersecting at a midpoint of each of the sets of the three lines and radially separated equidistantly;
     receiving a first selection in the additional Web content of one of the sets of three lines and third distributing yet further Web content presenting an astigmatism fan chart of thirty-six equidistantly arranged radii from a single vertex, the radii comprising a repeating sequence of lines of identical width to the selected one of the sets of three lines;

receiving a second selection in the yet further Web content of one of the radii and identifying a radial value for the second selection; and, presenting an eyeglass prescription including the visual acuity value, a cylinder value and an axis value, the cylinder and axis values deriving from the first and second selections.

12. The system of claim 11, wherein the communicative connection is established through a display of a Web page in a Web browser in the client computing device, the host computing system transmitting the Web page to the Web browser.

13. The system of claim 12, wherein the Web page includes a selectable user interface control for a pre-stored prescription and in response to receiving a selection of the control, retrieving a pre-stored eyeglass prescription including a pre-stored visual acuity value, pre-stored cylinder value and pre-stored axis value in lieu of presenting the acuity chart and the astigmatism clock chart to derive the visual acuity value, cylinder value and axis value.

14. The system of claim 12, further comprising presenting through the Web page, a video conferencing portal over which verbal directives are presented.

15. The system of claim 14, wherein the verbal directives include directives for standing at a specified distance from the Web content.

* * * * *